United States Patent [19]

Constantz

[11] Patent Number: 5,047,031
[45] Date of Patent: * Sep. 10, 1991

[54] IN SITU CALCIUM PHOSPHATE MINERALS METHOD

[75] Inventor: Brent R. Constantz, Woodside, Calif.

[73] Assignee: Norian Corporation, Mountain View, Calif.

[*] Notice: The portion of the term of this patent subsequent to Nov. 14, 2006 has been disclaimed.

[21] Appl. No.: 358,716

[22] Filed: May 30, 1989

Related U.S. Application Data

[63] Continuation-in-part of Ser. No. 183,770, Apr. 20, 1988, Pat. No. 4,880,610.

[51] Int. Cl.$^5$ ............................................. C01F 11/02
[52] U.S. Cl. ..................................... 606/77; 423/305; 423/309; 106/35
[58] Field of Search ............... 423/309, 313, 305, 317; 623/16, 901, 17; 433/199.1; 106/35; 606/77

[56] References Cited

U.S. PATENT DOCUMENTS

| | | | |
|---|---|---|---|
| 3,679,360 | 7/1972 | Rubin et al. | 23/109 |
| 3,787,900 | 1/1974 | McGee | 3/1 |
| 3,913,229 | 10/1975 | Driskell et al. | 32/15 |
| 4,097,935 | 7/1978 | Jarcho | 3/1.9 |
| 4,139,599 | 2/1979 | Tomlinson et al. | 423/308 |
| 4,157,378 | 6/1979 | Tomlinson et al. | 423/301 |
| 4,429,691 | 2/1984 | Niwa et al. | 128/92 C |
| 4,481,175 | 11/1984 | Iini et al. | 423/308 |
| 4,503,157 | 3/1985 | Hatahira | 501/1 |
| 4,518,430 | 5/1985 | Brown et al. | 433/199 |
| 4,612,053 | 9/1986 | Brown et al. | 106/35 |
| 4,659,617 | 4/1987 | Fujii et al. | 428/221 |
| 4,693,986 | 9/1987 | Vit et al. | 501/1 |
| 4,849,193 | 7/1989 | Palmer et al. | 423/308 |
| 4,880,610 | 11/1989 | Constantz | 423/305 |

FOREIGN PATENT DOCUMENTS

| | | | |
|---|---|---|---|
| 2755751 | 6/1978 | Fed. Rep. of Germany | 623/16 |
| 45-29578-R | 9/1970 | Japan | 423/313 |
| 53-110999 | 9/1978 | Japan | 623/16 |
| 143762 | 7/1985 | Japan | 423/307 |
| 62-132713-A | 6/1987 | Japan | 423/311 |
| 63-252913 | 10/1988 | Japan . | |
| 1331501 | 8/1987 | U.S.S.R. | 623/16 |

OTHER PUBLICATIONS

Lemaitre, Jacques et al., *Silicates Industriels* (1987) 9–10;141–146.

Arends and Jongebloed, "Apatite Single Crystals. Formation, Dissolution and Influence of $CO_3^{2-}$ Ions," *Recl. Trav. Chim. Pays-Bas* (1981) 100:3–9.

Chohayeb et al., "Evaluation of Calcium Phosphate as a Root Canal Sealer-Filler Material," *J. of Endodontics* (1987) 13(8):384–387.

Ohwaki et al., Abstracts of Poster Session at *The 13th Annual Meeting of the Society for Biomaterial*, p. 2, Presented Jun. 2–6, 1987, New York, New York.

*Primary Examiner*—Michael L. Lewis
*Assistant Examiner*—Peter T. DiMauro
*Attorney, Agent, or Firm*—Bertram I. Rowland

[57] ABSTRACT

Calcium phosphate minerals are formed by using phosphoric acid substantially free of uncombined water in conjunction with a calcium source, normally as any combination of carbonate, phosphate and hydroxide, and, as required, any additional base to neutralize the phosphoric acid. Protein may be optionally added. The resulting product is readily formed and then sets to a hard, stable, workable shaped object.

14 Claims, No Drawings

IN SITU CALCIUM PHOSPHATE MINERALS METHOD

CROSS-REFERENCE TO RELATED APPLICATIONS

This application is a continuation-in-part of U.S. Pat. Application Ser. No. 183,770 filed Apr. 20, 1988 now U.S. Pat. No. 4,880,610.

INTRODUCTION

1. Technical Field

The field concerns the preparation of calcium phosphate minerals and their applications.

2. Background

A number of calcium phosphate minerals, such as hydroxyapatite, fluorapatite, octacalcium phosphate (OCP), whitlockite (8-TCP), brushite and monetite, do, or may, find application as biocompatible minerals. The various crystalline forms have different properties which in particular applications may be more or less desirable. For example, OCP ($k_{sp} \cong 10^{-27}$) TCP ($\alpha$ or $\beta$ form) or $Ca_{3-x}Mg_x(PO_4)_2$ ($k_{sp} \cong 10^{-27}$) are resorbable, while brushite ($CaHPO_4 \cdot 2H_2O$) ($k_{sp} \cong 10^{-27}$) and monetite ($CaHPO_4$) ($k_{sp}$ $10^{-7}$) are very resorbable. (Brown and Chow, *Ann. Rev. of Materials Science* (1976) 6:213-236). By forming the different minerals with their varying crystalline structures, compositions and chemical and physical properties, mineral products may be obtained having different properties for particular applications.

Apatite is a general term for a wide range of compounds represented by the general formula $M^{2+}{}_{10}(ZO_4{}^{3-})_6Y^{-}{}_2$, wherein M is a metal atom, particularly alkali or alkaline earth metal atom, and $ZO_4$ is an acid radical, where Z may be phosphorus, arsenic, vanadium, sulfur or silicon, or may be substituted in whole or in part with carbonate ($CO_3{}^{2-}$). Y is an anion, usually halide, hydroxy, or carbonate.

Hydroxyapatite, as well as modified forms thereof, assumes substantial interest and importance by virtue of the fact that it is a major naturally occurring building block in bone, teeth, and some invertebrate skeletons. There are many situations where bone has been broken, destroyed, degraded, become too brittle, or been subject to other deteriorating effects. In many of these situations it would be desirable to be able to replace the bone structure or strengthen the bone structure. In providing materials to substitute for natural bone, there are a number of restraints on the nature and composition of the material.

The material should be physiologically acceptable, so as to avoid the initiation of clots, inflammatory response, and the like. Two different product forms are desirable: One being an hydroxy- or fluorapatite which is non-resorbable in vivo; the other including substantial amounts of carbonated apatite, calcium deficient apatite, OCP, TCP, brushite, and monetite, which are resorbable in vivo. In addition, the material must be strong and not friable. Furthermore, there should be strong adhesion between the material and any remaining bone. Also, desirably, the material should be subject to assuming some of the natural role of bone, such as accommodating stem cells, allowing remodelling by osteoclasts followed by new bone ingrowth, and normal metabolic calcium exchange of native bone.

Besides the biological and physiological considerations, there are the additional considerations of how the material is made and the ease with which it may be formed to a desired shape. Specifically, a material which could be injected as a liquid to fill voids and completely fill in areas deficient of hard bone is very desirable. Where the material is to be placed in situ, a variety of considerations come to the fore. For example, the rate at which the reaction occurs for formation of hydroxyapatite, as well as the change in enthalpy of the reaction, are important. Where the reaction is highly exothermic, it may not be tolerated by the patient. The form in which it is introduced must be stable in the environment in which it is introduced, so that not only must the final product be stable, but also the intermediate products as the reaction occurs.

It has therefore been found difficult to provide physiologically useful forms of hydroxyapatite and/or other calcium phosphate minerals. For the most part, the hydroxyapatites and other calcium phosphate bone grafting particulates which have been available have lacked one or more of the properties necessary for a useful implant, and, therefore, have failed to obtain general acceptance.

Relevant Literature

Patents of interest include U.S. Pat. Nos. 3,787,900; 3,913,229; 3,679,360; 4,097,935; 4,481,175; 4,503,157; 4,612,053; 4,659,617; and 4,693,986. See also, Arends and Jongebloed, *Rec. Trav. Chim. Pays-Bas* (1981) 100:3-9. Use of calcium phosphate as a sealer-filler material is described in Chohayeb et al., *J. Endodontics* (1987) 13:384-387. See also, Ohwaki et al., *13th Ann. Mtg. of the Soc. for Biomaterials*, June 2-6, 1987, New York, N.Y., p. 209.

SUMMARY OF THE INVENTION

Calcium phosphate minerals are prepared using highly concentrated phosphoric acid as a liquid or solid, substantially free of uncombined water, a source of an alkaline earth metal, particularly calcium, usually at least in part basic, optionally a base source other than a basic calcium source, a lubricant, such as water, and optionally hydroxyapatite crystals. The components are thoroughly mixed to provide a substantially uniform mixture, at which time the product may be shaped, followed by standing to form a solid mass and hardening to a final stable form. Ceramic fibers, proteins and/or organic polymers may be added to this product during mixing to give the final product specific material properties.

DESCRIPTION OF THE SPECIFIC EMBODIMENTS

Methods and compositions are provided for producing bone-like materials comprising structures analogous to the naturally occurring calcium phosphate minerals, particularly carbonated, fluoro- and hydroxyapatite. The products are readily formed by combining the reactants to provide a substantially uniform mixture, shaping the mixture as appropriate, and allowing the mixture to form a solid mass and harden. The reactants are for the most part a phosphoric acid source, substantially free of unbound water, an alkaline earth metal, particularly calcium, source, optionally crystalline nuclei, particularly calcium phosphate crystals, more particularly hydroxyapatite crystals, optionally, a source of base other than a basic calcium compound such as a calcium phosphate, particularly a calcium hydroxide, oxide and/or carbonate, and a lubricant such as water.

The dry ingredients may be pre-prepared as a mixture and combined with the liquid ingredients, under conditions where substantially uniform mixing occurs. Where gases evolve, the mixture is agitated, so as to provide for the release of any large pockets of gas. After a short mixing time period, the mixture is allowed to anneal while remaining quiescent, followed by an extended period of time of hardening.

By employing the subject procedures, compositions are obtained which have a wide variety of desirable properties for use in physiological purposes. The subject compositions are biocompatible having a pH in the range of about 5–8, usually in the range of about 6–7.5. They can be prepared, so that they can be administered at a temperature in the range of about 0°–45° C., usually 20°–40° C., and optimally about normal physiological temperature, 37° C. The composition has low or no toxicity when prepared in accordance with the subject invention, is substantially inactive, so far as detrimental interactions with various host components in vivo, and readily implantable. The implantation may be as a result of syringe or catheter injection, particularly the composition may be used as a paste which passes through a needle in the range of 10–18 gauge, preferably about 14–16 gauge. Alternatively, the composition is moldable, being capable of forming a clay-like putty which may be molded prior to setting.

The subject compositions also bond to other calcium phosphates when applied to a calcium phosphate surface, such as bones and teeth which are mainly hydroxyapatite and collagen. The composition is able to bond to surfaces which are wet or coated with blood, will fill voids, conforming with irregular surfaces, such as concavities and convexities. The composition may be applied as a continuous mass without the formation of fragments or loose particles to any significant degree. Furthermore, the subject compositions are found to be structurally compatible in providing for the structural functions of the replaced connective tissue.

The subject compositions may also be used as a delivery system, since the resorption rate in vivo may be varied by varying the mineralogy of the crystallized calcium phosphate minerals. In this manner, the subject compositions may provide for a wide range of rate of release of compounds having physiological properties. Compounds of interest may include various factors, such as bone morphogenic proteins, which may provide the implant similar inductive potential to a natural allograft or autograft of bone. Alternatively, various drugs may be employed in the composition, which may serve to prevent infection, attract blood cells, activate cells, and the like. The compositions may be modified by employing various natural or synthetic proteins, particularly polypeptides such as collagen, chitin, fibrin, heparin, etc. Alternatively, various materials may be included which may provide for x-ray opacity. For example, 10–30% by weight of bismuth oxide, barium sulfate, barium carbonate or zirconium oxide may be incorporated in the composition. For magnetic resonance imaging, various elemental isotopes may be employed for the composition, such as $^{19}F$, $^{31}P$, $^{18}O$, and $^{41}Ca$.

By the materials employed and their proportions, the compositions, during formation, handling, and as the final product may be varied widely as to their physical properties. The composition may be prepared at various degrees of fluidity, such as flowability or viscosity, by varying the amounts of lubricant employed, particularly water, or other hydroxylic compound, e.g., ethylene or polyethylene glycol. By using less liquid, or by the choice of other materials, the composition may be made less flowable and more formable, providing a consistency of modeling clay, so that the composition may be formed into a desired form.

The mechanical and physical properties of the final product may be varied widely. For example, the bulk porosity may be varied, depending on the particular ions which are used in the formation of the product. Also, microstructure may be varied, since the shapes and the size of the crystals can be varied with resulting variation in the mechanical properties of the product. Another parameter of interest is bulk permeability, since the permeability may be changed in relation to the particular application where a permeable or impermeable product may be desired. Also, the surface area may be varied, where a high surface area may be desirable, for example, greater than $10^2/gm$, to enhance protein bonding, particularly charged proteins.

The individual components in the reaction preparing the subject compositions will now be considered.

The phosphoric acid source may be varied. Depending upon the phosphoric acid source, the reaction may be exothermic, endothermic, or result in substantially no change in temperature of the mixture. A phosphoric acid source, greater than about 85% phosphoric acid, liquid or solid, amorphous or crystalline, should be substantially free of unbound water and may be polyphosphoric acid (116% phosphoric acid equivalents), 100% liquid phosphoric acid (prepared by heating phosphoric acid and phosphorus pentoxide), or 100% orthophosphoric acid crystals, anhydrous or hemihydrate, which may be dissolved in the reaction mixture in combination with added water. With the crystals, the crystals may be pre-mixed with the other dry ingredients for use with the aqueous base in preparing the subject product.

The calcium source may be varied, as to the anion, usually including in whole or at least in part carbonate. Usually, the carbonate will be present in at least about 30 formal percent, more usually at least about 60 formal percent, and generally at least about 90 formal percent. Depending upon the choice of anion, different effects will be observed as to the nature of the product. Anions which may be employed include carbonate, oxide, hydroxide, chloride, fluoride, phosphate, e.g. tetracalcium phosphate, which anions may be incorporated into the final product, etc. Calcium fluoride is relatively insoluble, so it will usually not be used as a source of fluoride. The oxides and hydroxides result in exothermicity and will be used sparingly. The hydroxide produces water and slows setting as well as providing exothermicity. Halide will generally be present in an amount not to exceed 0.2 mole of halide per mole of calcium.

In selecting the calcium source, particularly where the calcium source not only serves as a source of calcium, but also in its neutralizing capacity, it may also serve as a source of phosphate. Therefore, in providing the various combinations, one must consider what calcium phosphate product is desired, since for the most part, the resulting product will be dependent upon the ratio of calcium and phosphate in the mixture. For brushite and monetite, a 1:1 ratio is desired. For octacalcium phosphate, a 1.33:1 ratio is desired. For tricalcium phosphate, a 1.5:1 ratio is desired. For hydroxyapatite, a 1.67:1 ratio is desired. The particular mineral will also be affected by the pH, but since the pH of the mixture will generally be in the range of about 5-8, it is found that the calcium/phosphate ratio is overriding.

If desired, one may add small amounts of magnesium, which inhibits the formation of hydroxyapatite and favors the formation of a magnesium bearing form of tricalcium phosphate, called whitlockite. Desirably less than about ID mole percent of the calcium will be substituted by magnesium. Whitlockite has a substantially higher resorption rate as compared to hydroxyapatite, usually resorbing over a period of about several months to a year.

For addition of the halides, fluoride and chloride, to form fluorapatite or chlorapatite, respectively, various sources of fluoride and chloride may be employed. Normally, the sources will either be soluble salts, such as calcium chloride, sodium or calcium hexafluorosilicate ($Na_2$ or $CaSiF_6$) or sodium fluoride, or may be added as dilute acids in the aqueous lubricant, generally less than about 1 M. Usually at least about 5, more usually at least about 10% of the hydroxyl groups will be replaced, and up to 100%.

With carbonate as the anion, the reaction tends to result in little, if any, heat rise, but there is substantial evolution of gas, which gas must be released during the mixing. Fluoride and chloride serve to provide for a less resorbable product and a harder final product, in being included in the final crystal structure as fluorapatite or chlorapatite. Where a basic anion is used, such as carbonate hydroxide or phosphate, these anions will serve to at least partially neutralize the phosphoric acid.

As required, additional base will be added to neutralize the phosphoric acid. Normally, at least about 90% of stoichiometric of base will be provided for neutralization of the acid. Desirably the pH of the product in water will be in the range of about 5 to 9. By stoichiometric is intended available base, and not equivalence. That is, not all of the carbonate will be available for neutralization and, in some instances, it will be desirable to retain a proportion of the product as carbonate, rather than as phosphate. Thus, in determining the amount of additional neutralizing capacity, the amount of hydroxide, oxide or $Ca_4(PO_4)_2O$ employed will be calculated based on how much carbonate is to be retained in the product. The neutralizing capacity will be desirably basic phosphates, although alkali or alkaline earth metal hydroxide, more particularly sodium or potassium, or combinations thereof, may be used. In choosing the various cations and anions, consideration must always be given as to whether the particular ion will be retained in the product and its effect on physiologic acceptance and product properties. For the most part, the total concentration of alkali metals should be kept to a minimum.

The next ingredient is optional and is calcium mineral nuclei, particularly hydroxyapatite. The source of the nuclei may be any physiologically acceptable source, such as ground bone, where the bone will be freed of undesirable organic matter, which could cause an immune or inflammatory reaction. The nuclei will generally be of a size in the range of about 1 mm to 10 Å, more usually 1 $\mu$m to 0.1 $\mu$m. Hydroxyapatite nuclei useful for the subject invention are commercially available, for example BioGel HTP, DNA Grade, from Bio-Rad.

The water which is used will be substantially pure, such as double distilled, deionized, or equivalent thereof. Other hydroxylic materials which are water miscible, pharmacologically acceptable and do not interfere with the calcium phosphate formation, may also find use.

In many situations it may be desirable to include various bone associated proteins to modify the physical properties of the composition, enhance resorption, angiogenesis, cell entry and proliferation, mineralization, bone formation, growth of osteoclasts and/or osteoblasts, or the like. Proteins of particular interest are the different types of collagen, particularly Type I. Other proteins include osteonectin, sialoproteins (BSP), $\alpha$-2HS-glycoproteins, bone-Gla-protein (BGP), matrix-Gla-protein, bone phosphoglycoprotein, bone phosphoprotein, bone proteoglycan, proteolipids, bone morphogenetic protein, cartilage induction factor, platelet derived growth factor, and skeletal growth factor. Other proteins associated with other parts of human or other mammalian anatomy, include proteins associated with cartilage, such as chondrocalcining proteins associated with dentin, such as phosphophoryn, glycoproteins and Gla proteins; associated with enamel, such as amelogenin, and enamelin.

Other proteins of interest include fibrin, fibrinogen, kerating tubulin, elastin and the like. Blood proteins may be employed, individually or together in plasma or serum.

While the ingredients can be added individually, desirably, the dry ingredients may be combined for subsequent combination with the wet ingredients. Thus, where orthophosphoric acid crystals are employed, these may be combined with a calcium source, and combined in appropriate proportions and mixed thoroughly to provide a dry uniform powder. The dry mixture may then be added to the aqueous base for reaction.

The amount of phosphoric acid will generally be about 6 to 15 parts, more usually from about 8 to 12 parts by weight. The calcium source will generally be from about 6 to 15, more usually from about 8 to 12 parts, generally not differing by more than about 0.8-1.2 parts per part of phosphoric acid source. Particularly, where calcium carbonate and calcium hydroxide are employed, generally, the ratio of calcium carbonate to calcium hydroxide by weight will be about 4-10:1, more usually 5-8:1.

The calcium mineral crystal nuclei, if present, will generally vary from about 0.2 to 10 parts, more usually from about 0.5 to 6 parts by weight.

The amount of neutralizing capability or base which is employed will be dependent upon the amount of neutralization which is provided as the calcium source. Generally, the amount which is employed will vary from about 0.1 to 7 parts, more usually from about 1 to 6 parts.

The amount of water which is used, conveniently as the solvent for the neutralizing agent(s), will generally be from about 15 to 50, more usually from about 20 to 35 weight percent of the entire composition. The amount of water which is employed should be considered in light of the amount of calcium hydroxide which is employed, which produces water in the neutralization of the phosphoric acid.

Various additional components may be included during the formation of the calcium phosphate mineral. Of particular interest are proteins involved in skeletal structure. The protein may be added in from about 0.2 to 2 parts of protein as an aqueous dispersion or solution. Usually, the protein will be present in from about 1-10 wt % of the aqueous dispersion. The amount of water added as the protein dispersion will be added in addition to the water of the aqueous base, where the total amount of water will come within the above limitations.

Various additives may be included to modify the physical structure. Various water soluble physiologically acceptable materials may be included in minor amount. Sugars, such as sucrose, glucose or fructose, may be included to enhance porosity. The weight of the sugar will usually not exceed 5 wt % of the total solids.

The product is formed by combining the dry ingredients, either separately or pre-mixed, with the phosphoric acid and the aqueous media, neutralizing agent(s), protein, and other additives, as appropriate. The mixture is thoroughly mixed over a relatively short time, so as to thoroughly distribute all of the reactants. Once the mixture is uniformly dispersed, the mixture may then be kneaded, continuing the process of reaction, releasing any gas which is formed, and shaping the product into an appropriate form. The kneading is over a relatively short time, usually not less than about 0.5 minutes and not more than about 5 minutes, usually not more than about 2 minutes. Where the product is to be introduced in situ, it may be injected into the appropriate site, using a syringe or catheter, or packed in by other means, as appropriate.

The product is now allowed to set, during which time crystals grow and the product becomes an integral mass. While the product may harden almost immediately, usually the maturing process should take at least about 10 minutes, usually at least about 15 minutes, and not more than about 30 minutes, usually not more than about 25 minutes. Alternatively, where the material has been introduced at a site where it is to be retained, the material will naturally harden over time.

The subject products may be used for a variety of purposes, such as any form of connective tissue replacement, including bone cement, an injected prosthetic implant, a prosthetic orthopaedic or dental implant, as a root canal filler, a prophylactic injection to augment weak osteoporotic bone, or a vehicle for drug delivery. The composition may be used as a paste, being applied to a surface for adherence or holding some structure in place.

The subject compositions may be used with other materials to provide for specific types of properties. For example, fibrous materials may be employed, both organic and inorganic, such as silicon carbide whiskers, hydroxyapatite fibers, metallic fibers, or the like. See, for example, U.S. Pat. No. 4,503,157.

Alternatively, various fillers may be employed, which may change the density of the material, add additional tensile strength, provide for enhanced flexibility, or the like. Where a porous structure is desired, various additives may be included which may be leached out, so as to provide for porosity in the mixture, in addition to any porosity achieved with the release of the gas formed during the reaction to produce the product. Porosity may also be achieved by the particular anions and cations employed, where alkali metal salts are produced which are readily dissolved in the medium in which it is allowed to harden. Thus, by using calcium chloride and sodium or potassium hydroxide, the resulting salt will be water soluble and its dissolution will result in pathways through the structure. Similarly, one may include various water soluble fibers, particles, or the like, in the composite structure, which may also be leached out to provide for porosity. Thus, the method of preparation allows for varying the characteristics of the final product.

The viscosity of the product may be varied depending on the application. The more basic the product (higher Ca/P ratio) the more the product will be hydroxyapatite, while the more acidic the product, the more the product will approach the properties of brushite. By varying the product crystal structure, percentage of solids, and presence of other additives, the viscosity may be selected to allow for ease of administration to the site to be treated.

Various considerations are associated with the physical characteristics of the product. Porosity may be increased by increasing the amount of lubricant in the paste, which occupies space in the final product, leaving behind a void or pore. Gas evolution from the paste may also create voids in the crystallizing product. Thus, porosity may be controlled by adjusting the amount of lubricant and gas evolution. For example, with calcium carbonate as a calcium source, porosity may be reduced by using dilute hydrochloric acid as the lubricant, where the reaction of the acid with the carbonate will result in gas evolution before the paste thickens. Thus, the $CO_2$ will be lost before the formation of the product, resulting in low porosity, while there will be little if any carbonate, to become incorporated into the final product. In general, as porosity increases, the compressive strength of the crystallized material decreases.

Porosity will not be the only parameter associated with compressive strength. Depending upon the other anions present in the final composition, compressive strength may vary by more than order of magnitude, while still having about the same porosity. For example, a typical fluorapatite with 45% porosity may have a compressive strength of 1,000 psi, whereas a carbonate apatite may have a compressive strength of 10,000 psi. Generally, fluorapatite have amorphous crystal morphologies, while carbonated apatite generally has needle-like crystal morphologies.

Substantial changes in physical properties will be obtained by the addition of biopolymers such as collagen or other naturally-occurring structural protein. When adding collagen to the paste by being present in the water solution, the crystallography of the final product is substantially unaffected, while the mechanical properties vary distinctively. The material appears viscoelastic, rather than having linear elasticity and brittleness, and appears to be more abrasion resistant.

Kits may be provided to prepare the subject compositions. Thus, various of the ingredients may be premixed to form a powder which may then be combined with the phosphoric acid source and lubricant to provide the final product. Generally, the kit may be comprised of the calcium source, which will include at least calcium carbonate, desirably tetracalcium phosphate, and to varying degrees, calcium oxide and/or hydroxide. These may be ground together to form a uniform mixture, where the particle size is not critical to this invention. Where other anions are to be included, the mixture may also include a source of halide salt.

In a separate vessel, the phosphoric acid source will be provided, conveniently as crystals, or as phosphoric acid of at least about 100% substantially free of uncombined water.

The following examples are offered by way of illustration and not by way of limitation.

EXPERIMENTAL

Example 1

SB 110

An alkaline solution was prepared of 4.5 g of sodium hydroxide pellets in 15.0 ml of distilled water. A powder was prepared of 9.8 g of orthophosphoric acid crystals, 8.0 g of calcium carbonate, 1.5 g of calcium hydroxide, and 5.0 g of hydroxyapatite crystal nuclei. The powders were mixed and ground together until thoroughly dispersed. The 15 ml of sodium hydroxide solution was poured into the mixed powders and mixed for about 1 to 2 min until a paste was formed. The mixture was formed into the desired shape and was then allowed to anneal for about 20 min, without being disturbed.

The product prepared as described above has the following characteristics:

The mixture anneals to a hard, polycrystalline, ceramic-like material.

X-ray diffraction (XRD) analysis of the material shows it to contain the following mineral phases:
1) Brushite (dibasic calcium phosphate, dihydrate)—$CaHPO_4.2H_2O$;
2) Monetite (dibasic calcium phosphate) —$CaHPO_4$;
3) Octacalcium phosphate—$Ca_8H_2(PO_4)_6.5H_2O$.

Example 2

B74/B74-W

An alkaline solution was prepared of 5.4 g of sodium hydroxide pellets in 19.0 ml of distilled water. A powder was prepared of 9.8 g of orthophosphoric acid crystals, 8.0 g of calcium carbonate, 1.5 g of calcium hydroxide, and 5.0 g of hydroxyapatite crystal nuclei. The powders were mixed and ground together until thoroughly dispersed. The 19 ml of sodium hydroxide solution was poured into the mixed powders and mixed for about 1 to 2 min until a paste was formed. Some of the paste mixture was loaded into a 5 ml syringe and ejected from the syringe through a 14-gauge cannula to form ribbons of the paste. Some of the mixture was formed by hand into a desired shape. The material was then allowed to anneal for about 20 min, without being disturbed. After annealing, some of the ribbon was placed in tap water to soak (B74-W).

The products prepared as described above have the following characteristics:

When initially mixed it is a paste which can be ejected through a standard syringe. Subsequent batches of this mixture have been injected into rats subcutaneously, intramuscularly and also into the intermedullary canal of rat femurs.

The mixture anneals to a hard, polycrystalline, ceramic-like material.

X-ray diffraction (XRD) analysis of the material which was not placed in water shows it to contain the following mineral phases:
1) Calcite—$CaCO_3$;
2) Hydroxyapatite—$Ca_5(PO_4)_3(OH)$;
3) Dibasic Sodium Phosphate, dihydrate—$Na_2HPO_4.2H_2O$;
4) Sodium Bicarbonate—$NaHCO_3$.

X-ray diffraction (XRD) analysis of the material which was placed in water shows it to contain the following mineral phases:
1) Calcite—$CaCO_3$;
2) Hydroxyapatite—$Ca_5(PO_4)_3(OH)$.

Example 3

SB w/BioFibre TM

An alkaline solution was prepared of 5.4 g of sodium hydroxide pellets in 19.0 ml of distilled water. A powder was prepared of 9.8 g of orthophosphoric acid crystals, 8.0 g of calcium carbonate, 1.5 g of calcium hydroxide, and 5.0 g of BioFibre TM (microcrystalline hydroxyapatite fibers). The powders were mixed and ground together until thoroughly dispersed. The 19 ml of sodium hydroxide solution was poured into the mixed powders and mixed for about 1 to 2 min until a paste was formed. The mixture was formed into the desired shape, and was then allowed to anneal for about 20 min, without being disturbed.

The products prepared as described above have the following characteristics:

The mixture anneals to a hard, polycrystalline, ceramic-like material, which feels stiffer than the material produced in Example 2.

EXAMPLE 4

SB w/Collagen

A slurry was prepared containing 0.6 g of collagen for each 13.6 g of distilled water, and heated at 35° C. for 1-2 days. An alkaline solution was prepared of 5.4 g of sodium hydroxide pellets in 5.4 g of distilled water. A powder was prepared of 9.8 g of orthophosphoric acid crystals, 8.0 g of calcium carbonate, 1.5 g of calcium hydroxide, and 5.0 g of hydroxyapatite crystal nuclei. The powders were mixed and ground together until thoroughly dispersed, and then 14.2 g of the collagen slurry was poured into the powders, followed by the 10.8 g of sodium hydroxide solution. The solutions were mixed into the powders for about 1 to 2 min until a paste was formed. The mixture was formed into the desired shape, and was then allowed to anneal for about 20 min, without being disturbed.

The products prepared as described above have the following characteristics:

The mixture anneals to a hard, polycrystalline, ceramic-like material, which is tougher and more viscoelastic than the material produced in Example 2 (B74 recipe) and Example 3 (BioFibre TM recipe).

The compositions of the subject invention provide for a number of desirable properties. The compositions will set in a moist environment, for example, saliva, so that the compositions may be used for various purposes in the mouth. In addition, the subject compositions will set up and bond to a substrate in the presence of a substrate of bone serum, bone marrow and blood, where strong bonding characteristics are achieved between the underlying bony substrate and the subject compositions. In addition, no significant dimensional changes occur with the product during crystallization. Thus, one may form the product while moldable and the final form will have substantially the same dimensions. If some expansion is desired, one may use a gas evolving calcium source, so that the gas expansion provides for some expansion of the composition. Direct mechanical apposition is possible because of the injectable and moldable quality of the paste before it crystallizes. Chemical apposition to bone occurs because as the paste forms in direct contact with like mineralogies of connective tissues, direct chemical bonds form between the implant the bone. Since the subject compositions are biocompatible, bone grows up to the implant and interdigitates with it.

The setting time can be varied by varying the amount of lubricant employed. Employing different calicum sources can also have an effect on the rate of hardening, as well as the nature of the final product. The temperature of the reaction for the formation of the subject composition and temperature at which it may be introduced in vivo is controllable by the particular choice of components. By varying the choice of phosphoric source and calcium source, the reaction may be endothermic, exothermic, or may be engineered to set up at room temperature or at body temperature (37° C.). In addition, for convenience, the product may be provided as a kit, with the individual components may be gamma-sterilized at 3.5 MPa. If desired, alografted bone chips may be placed in the material to provide the product with bone inductive properties after mixing in vivo.

It is evident from the above results, that the subject methods and compositions provide a unique alternative to other methods for producing hydroxyapatite. In accordance with this method, compositions can be produced which can be allowed to harden in situ, so as to be placed in position and fill any spaces. The mixture will then harden to a shaped product which may then be modified, if desired, to fit a particular site, so that it may be machined, worked, or otherwise formed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for making calcium phosphate minerals comprising:
    combining phosphoric acid, substantially free of uncombined water, a calcium source, neutralizing anions including at least one of carbonate, phosphate and hydroxide in an amount sufficient to substantially neutralise said phosphoric acid and water in an amount to provide a kneadable mixture;
    agitating the mixture to produce a substantially uniform mixture; and
    allowing the substantially uniform mixture to set and become annealed to a hard workable structure.

2. A method according to claim 1, wherein calcium phosphate crystals are combined in said combining step.

3. A method according to claim 1, wherein said phosphoric acid is orthophosphoric acid crystals.

4. A method according to claim 3, wherein the dry ingredients, orthophosphoric acid and calcium source are premixed prior to combining with the water or the calcium source and water are precombined prior to combining with said phosphoric acid.

5. A method according to claim 1, wherein said calcium source is present at least in part as calcium carbonate.

6. A method according to claim 1, wherein a protein is combined in said combining step.

7. A method for making hydroxyapatite comprising:
    combining orthophosphoric acid crystals, a neutralizing source comprising at least one of calcium carbonate, alkali metal hydroxide, calcium hydroxide or calcium phosphate, in an amount to provide a substantially neutral product, and water in an amount to provide a kneadable mixture;
    agitating the mixture to produce a substantially uniform mixture; and
    allowing the substantially uniform mixture to set and become matured to a hard workable structure.

8. A method according to claim 7, wherein said orthophosphoric acid crystals and neutralizing source are precombined in a uniform mixture.

9. A method according to claim 8, wherein said orthophosphoric acid crystals are present in 6–15 parts by weight, and said calcium carbonate is present in from about 6–15 parts by weight.

10. A method according to claim 7, wherein said maturing occurs in situ in bone.

11. A method according to claim 7, wherein a source of fluoride or chloride is included in said mixture to displace at least 10% of the hydroxyl groups of hydroxyapatite.

12. A method according to claim 11, wherein $CaSiF_6$, $Na_2SiF_6$, $NaF$ or $CaCl_2$ is included in said mixture to displace at least 10% of the hydroxyl groups of said hydroxyapatite.

13. A method according to claim 7, wherein 0.2–2 parts of collagen is combined in said combining step.

14. A method according to claim 7, wherein dilute HF or HCl of less than about 1M are included with a carbonate anion calcium source, wherein said HF or HCl are in sufficient amount to displace at least 10% of the hydroxyl groups of said hydroxyapatite.

* * * * *